United States Patent [19]

Habeeb et al.

[11] Patent Number: 5,055,211
[45] Date of Patent: Oct. 8, 1991

[54] LUBRICATING OIL CONTAINING A MIXED LIGAND METAL COMPLEX AND A METAL THIOPHOSPHATE

[75] Inventors: Jacob J. Habeeb, Westfield, N.J.; Gopal H. Singhal, Baton Rouge, La.

[73] Assignee: Exxon Research and Engineering Company, Florham Park, N.J.

[21] Appl. No.: 404,132

[22] Filed: Sep. 7, 1989

[51] Int. Cl.$^5$ ................ C10M 135/18; C10M 137/10
[52] U.S. Cl. .............................. 252/42.7; 252/32.7 E; 252/75
[58] Field of Search ................ 252/32.7 E, 32.7 HC, 252/33.6, 42.7, 45, 46.4, 49.7

[56] References Cited

U.S. PATENT DOCUMENTS

| | | | |
|---|---|---|---|
| 3,252,910 | 5/1966 | Oberright | 252/42.7 |
| 3,356,702 | 12/1967 | Farmer et al. | 252/42.7 |
| 3,462,367 | 8/1969 | Booher | 252/42.7 |
| 3,840,463 | 10/1974 | Froeschmann et al. | 252/42.7 |
| 4,395,343 | 7/1983 | de Vries et al. | 252/32.7 E |
| 4,849,123 | 7/1989 | Tipton et al. | 252/42.7 |

OTHER PUBLICATIONS

Smalheer and Smith, "Lubricant Additives" Lezius–Hiles Co. Ed. p. 1-11 (1967).
Gable, R. W., Raston, C. L., Rowbottom, G. L., White, A. H. Winter, G., Preparation, Properties, and Structure of Bis . . . , J.C.S. Dalton, pp. 1392-1397.
Hoskins, B. F., Tiekink, E. R. T., Winter, G., The Preparation and Characterization of Mixed Dithiolate Ligand Complexes . . . , Inorganica Chimica Acta, 105 (1985), pp. 171-176.
Tsipis, C. A., Hadjikostas, C. C., Manoussakis, G. E., Mixed-Ligand Iron (III) Dithiocarbamates, Calculation of Ligand . . . , Inorganica Chimica Acta, 23 (1977), pp. 163-171.
Mohammed, T. J., Mustafa, I. A., Al-Mukhtar, S. E., Metal Complexes with Sulfur Donor Ligands . . . , J. Indian Chem. Soc., vol. LXII, Oct. 1985, pp. 725-728.

Primary Examiner—Prince E. Willis
Assistant Examiner—E. McAvoy
Attorney, Agent, or Firm—John W. Ditsler

[57] ABSTRACT

The addition of certain mixed ligand metal complexes and a metal thiophosphate to a lubricating oil results in a significant improvement in the anti-wear performance of the oil. Tin dithiocarbamate-ethoxyethylxanthate and zinc dialkyldithiophosphate are preferred additives.

31 Claims, 2 Drawing Sheets

LUBRICATING OIL CONTAINING A MIXED LIGAND METAL COMPLEX AND A METAL THIOPHOSPHATE

BACKGROUND OF THE INVENTION

1. Field of the Invention

This invention relates to a lubricating oil composition having improved antiwear performance due to the presence of a mixed ligand metal complex and a metal thiophosphate.

2. Description of Related Art

Engine lubricating oils require the presence of additives to protect the engine from wear. For almost forty years, the principal antiwear additive for engine lubricating oils has been zinc dialkyldithiophosphate (ZDDP). However, ZDDP must be used in concentrations of 1.4 wt. % or greater to be effective. Since phosphates may result in the deactivation of emission control catalysts used in automotive exhaust systems, a reduction in the amount of phosphorus-containing additives (such as ZDDP) in the oil would be desirable. In addition, ZDDP alone does not provide the enhanced antiwear protection necessary in oils used to lubricate today's small, high performance engines.

Certain mixed ligand metal complexes are known. For example, U.S. Pat. No. 4,308,154 discloses the use of mixed metal salts of dialkylphosphorodithioic acids and carboxylic acids in lubricating oils. Mixed ligand metal complexes have also been described in the literature (see C. A. Tsipis et al., "Mixed Ligand Iron (III) Dithiocarbamates", *Inorg. Chem. Acta.*, 23, p. 163 [1977]; R. W. Gable et al., "Preparation, Properties, and Structure of Di-μ-thio-bis[bis(O-ethyl dithiocarbonato] tin (IV)" J. C. S. Dalton, p. 1392 (1981), and B. F. Hoskins et al., "The Preparation and Characterization of Mixed Dithiolate Ligand Complexes", *Inorg. Chem. Acta*, 105, p. 171 (1985)). Adding physical mixtures of various ligands to lubricating oils are also known (see, for example, U.S. Pat. Nos. 4,171,268; 4,395,343; and 4,402,840).

However, none of these publications suggest that the antiwear performance of a lubricating oil can be enhanced when certain mixed ligand metal complexes and a metal thiophosphate are present therein.

SUMMARY OF THE INVENTION

This invention concerns a lubricating oil containing antiwear reducing amounts of certain mixed ligand metal complexes and a metal thiophosphate. More specifically, we have discovered that the antiwear performance of a lubricating oil is enhanced when the oil contains a minor amount of (a) at least one mixed ligand metal complex selected from the group consisting of
(i) a metal dithiophosphate-alkylxanthate complex,
(ii) a metal dithiophosphate-dithiocarbamate complex,
(iii) a metal dithiocarbamate-alkylxanthate complex,
and mixtures thereof; and
(b) a metal thiophosphate.

Bis-(dibutyldithiocarbamato diethoxyethylxanthato) tin (IV) and zinc dialkyldithiophosphate are preferred additives.

DETAILED DESCRIPTION OF THE INVENTION

Figure 1:
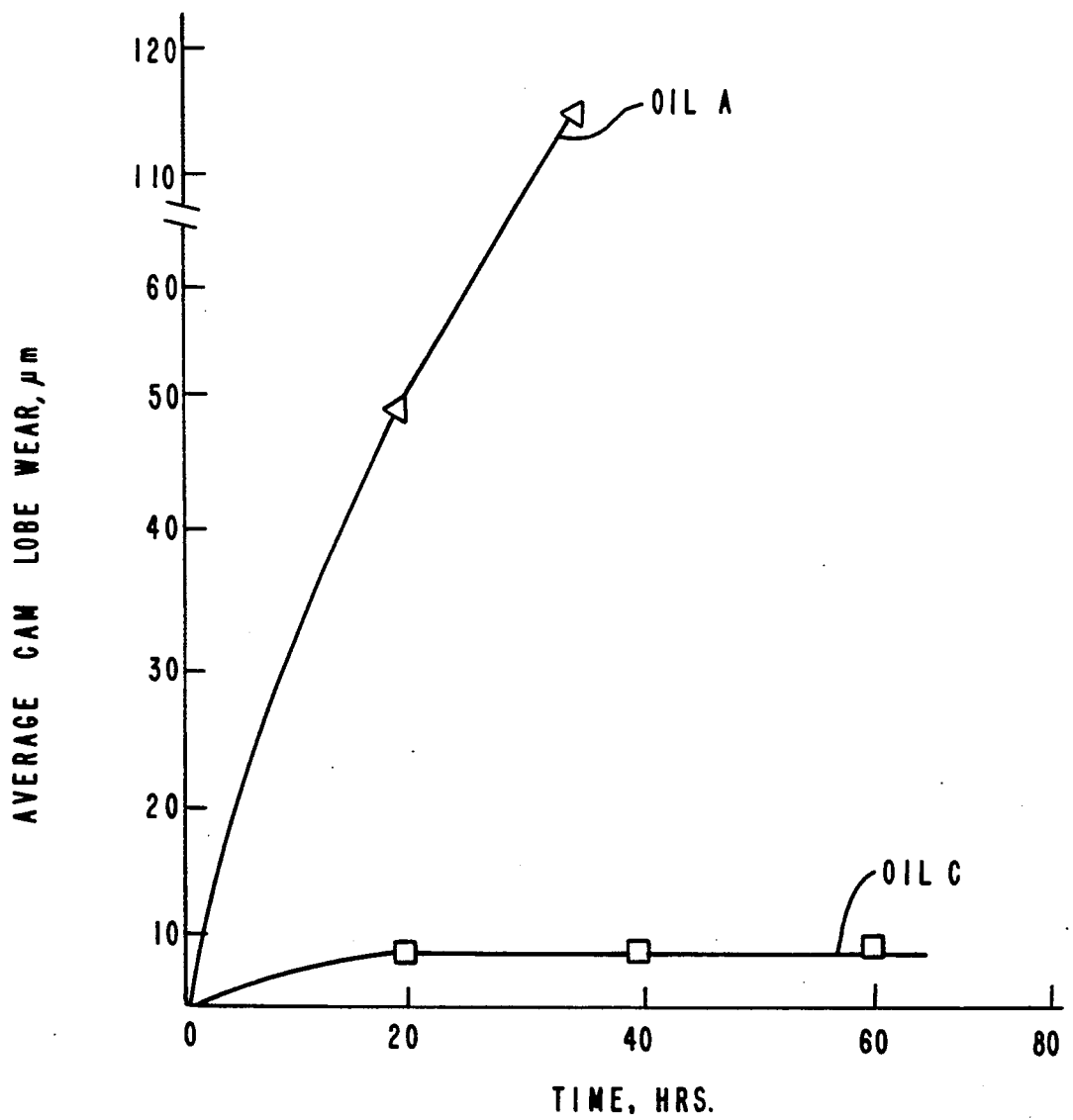
FIGS. 1 and 2 are each graphs of average cam lobe wear versus time for two different oil formulations.

In one embodiment, this invention concerns a lubricating oil composition comprising
(a) a lubricating oil basestock,
(b) a mixed ligand metal complex comprising at least one member selected from the group consisting of
(i) a metal dithiophosphate-alkylxanthate complex,
(ii) a metal dithiophosphate-dithiocarbamate complex,
(iii) a metal dithiocarbamate-alkylxanthate complex,
and mixtures thereof; and
(c) a metal thiophosphate In another embodiment, this invention concerns a method for reducing the wear of an internal combustion engine by lubricating the engine with an oil containing an oil soluble additive system which comprises at least one of the mixed ligand metal complexes mentioned above and a metal thiophosphate.

In general, the lubricating oil will comprise a major amount of a lubricating oil basestock (or base oil) and a minor amount of an additive system which contains at least one of the mixed ligand metal complexes mentioned above and a metal thiophosphate. If desired, other conventional lubricating oil additives may be present in the oil as well.

The lubricating oil basestock can be derived from natural lubricating oils, synthetic lubricating oils, or mixtures thereof. In general, the lubricating oil basestock will have a kinematic viscosity ranging from about 5 to about 10,000 cSt at 40° C., although typical applications will require an oil having a viscosity ranging from about 10 to about 1,000 cSt at 40° C.

Natural lubricating oils include animal oils, vegetable oils (e.g., castor oil and lard oil), petroleum oils, mineral oils, and oils derived from coal or shale.

Synthetic oils include hydrocarbon oils and halo-substituted hydrocarbon oils such as polymerized and interpolymerized olefins (e.g. polybutylenes, polypropylenes, propylene-isobutylene copolymers, chlorinated polybutylenes, poly(1-hexenes), poly(1-octenes), poly(1-decenes), etc., and mixtures thereof); alkylbenzenes (e.g. dodecylbenzenes, tetradecylbenzenes, dinonylbenzenes, di(2-ethylhexyl)benzene, etc.); polyphenyls (e.g. biphenyls, terphenyls, alkylated polyphenyls, etc.); alkylated diphenyl ethers, alkylated diphenyl sulfides, as well as their derivatives, analogs, and homologs thereof; and the like.

Synthetic lubricating oils also include alkylene oxide polymers, interpolymers, copolymers and derivatives thereof wherein the terminal hydroxyl groups have been modified by esterification, etherification, etc. This class of synthetic oils is exemplified by polyoxyalkylene polymers prepared by polymerization of ethylene oxide or propylene oxide; the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic carboxylic esters thereof (e.g., the acetic acid esters, mixed $C_3$–$C_8$ fatty acid esters, and $C_{13}$ oxo aciddiester of tetraethylene glycol).

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, and the like.

Silicon-based oils (such as the polyakyl-, polyaryl-, polyalkoxy-, or polyaryloxy-siloxane oils and silicate oils) comprise another useful class of synthetic lubricating oils. These oils include tetraethyl silicate, tetraisopropyl silicate, tetra-(2ethylhexyl) silicate, tetra-(4-methyl-2-ethylhexyl) silicate, tetra(p-tert-butylphenyl) silicate, hexa(4-methyl-2-pentoxy)-disiloxane, poly(methyl)-siloxanes and poly(methylphenyl) siloxanes, and the like. Other synthetic lubricating oils include liquid esters of phosphorus-containing acids (e.g., tricresyl phosphate, trioctyl phosphate, diethyl ester of decylphosphonic acid), polymeric tetrahydrofurans, polyalphaolefins, and the like.

The lubricating oil may be derived from unrefined, refined, rerefined oils, or mixtures thereof. Unrefined oils are obtained directly from a natural source or synthetic source (e.g., coal, shale, or tar sands bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

The mixed ligand metal complexes used in this invention will have the following general formulas (a) the metal dithiophosphate-alkylxanthate complex

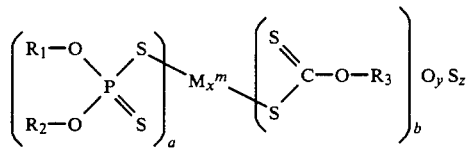

(b) the metal dithiophosphatedithiocarbamate complex

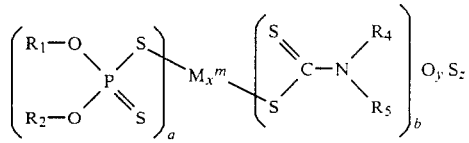

(c) the metal dithiocarbamate-alkylxanthate complex

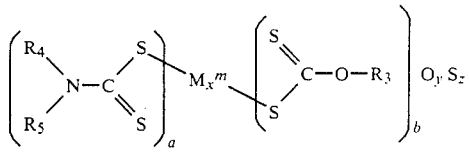

where $R_1$, $R_2$, $R_3$, $R_4$ and $R_5$ are each an alkyl group (straight, branched, or cyclic); an alkoxy substituted alkyl group; a polyalkoxy substituted alkyl group; an aryl group; or a substituted aryl group, and M is a metal.

a is an integer from 1 to 5.

b is an integer from 1 to 5.

m is the oxidation state of the metal.

x is 1.

y+z is an integer from 0 to 4.

Preferably, at least one (and more preferably all) of $R_1$, $R_2$, $R_3$, $R_4$, and $R_5$ is a straight alkyl group, a branched alkyl group, or an alkoxy substituted alkyl group. More preferably, at least one (and most preferably all) of $R_1$-$R_5$ is a straight chained alkyl group. Although the number of carbon atoms in $R_1$, $R_2$, $R_3$, $R_4$, and $R_5$ could vary broadly, typically at least one will have from 1 to 24, preferably from 2 to 12, and more preferably from 2 to 8, carbon atoms. Preferably, $R_1$-$R_5$ will have from 1 to 24 carbon atoms. In addition, the combination of R groups in each mixed ligand metal complex should contain a sufficient number of carbon atoms such that the complex is soluble in the oil. Examples of suitable substituted groups that can be included in the R groups include alkyl, aryl, hydroxy, alkylthio, amido, amino, keto, ester groups, and the like.

M can be a variety of metals, but, in general, will comprise a metal selected from the group consisting of antimony, bismuth, copper, iron, indium, molybdenum, tin, titanium, and zinc. Preferred metals are antimony, molybdenum, tin, and zinc, with molybdenum and tin being particularly preferred. Tin is most preferred.

m is the oxidation state of M and, typically, will be an integer ranging from 2 to 6, preferably from 2 to 4. Similarly, a, b, x, y, and z are integers whose values will vary as shown in Table 1 below.

TABLE 1

| m | a | b | x | y + z |
|---|---|---|---|-------|
| 2 | 1 | 1 | 1 | 0 |
| 3 | 1,2 | 1,2 | 1 | 0,1 |
| 4 | 1-3 | 1-3 | 1 | 1,2 |
| 5 | 1-4 | 1-4 | 1 | 0-3 |
| 6 | 1-5 | 1-5 | 1 | 0-4 |

Examples of the various xanthate groups that can be used in the mixed ligand metal complexes of this invention are (1) alkyl xanthates such as methyl xanthate, ethyl xanthate, propyl xanthate, butyl xanthate, amyl xanthate, hexyl xanthate, cyclohexyl xanthate, octyl xanthate, decyl xanthate and dodecyl xanthate, isopropyl xanthate, isobutyl xanthate, 2-ethylhexyl xanthate, or mixtures thereof, and the like; and (2) alkoxyalkylxanthates such as methoxyethylxanthate, ethoxyethylxanthate, phenoxyethylxanthate, isopropyloxyethylxanthate, ethoxyethoxyethylxanthate, 2-ethylhexyloxyxanthate, or mixtures thereof, and the like.

Preferred alkyl xanthates are butyl xanthate, amyl xanthate, octyl xanthate, decyl xanthate, dodecyl xanthate, 2-ethylhexyl xanthate, and cyclohexyl xanthate, diamyl xanthate, or mixtures thereof. Butyl xanthate, octyl xanthate, decyl xanthate, diamyl xanthate, 2-ethylhexyl xanthate, or their mixtures are particularly preferred, with diamyl xanthate being most preferred. Preferred alkoxyalkylxanthates are ethoxyethylxanthates, ethoxyethylxanthate, butoxyethylxanthate, 2-ethylhexyloxyxanthate, or mixtures thereof, with ethoxyethylxanthate and butoxyethylxanthate being particularly preferred.

Examples of the various dithiophosphates that can be used in the mixed ligand metal complexes of this invention are dimethyl dithiophosphate, diethyl dithiophosphate, dipropyl dithiophosphate, dibutyl dithiophosphate, diamyl dithiophosphate, dioctyl dithiophosphate, di-2-ethylhexyl dithiophosphate, diisobutyl dithiophosphate, isobutyl, butyl dithiophosphate, diisopropyl dithiophosphate, didodecyl dithiophosphate, or mixtures thereof, and the like. Preferred dithiophosphates are diethyl dithiophosphate, dibutyl dithiophosphate, diamyl dithiophosphate, dioctyl dithiophosphate, di-2-ethylhexyl dithiophosphate, isobutyl, butyl dithiophosphate, or mixtures thereof, with diethyl dithiophosphate, dibutyl dithiophosphate, di-2-ethylhexyl dithiophosphate, diisobutyl dithiophosphate, isobutyl dithiophosphate, butyl dithiophosphate, or their mixtures, being particularly preferred. Diethyl dithiophosphate is most preferred.

Examples of the various dithiocarbamate groups in the mixed ligand metal complexes of this invention are dimethyl dithiocarbamate, diethyl dithiocarbamate, dipropyl dithiocarbamate, diisopropyl dithiocarbamate, dibutyl dithiocarbamate, diisobutyl dithiocarbamate, dipentyl dithiocarbamate, dihexyl dithiocarbamate, dicyclohexyl dithiocarbamate, diphenyl dithiocarbamate, dibenzyl dithiocarbamate, diethylphenyl dithiocarbamate, di-2-ethylhexyl dithiocarbamate, dimethylphenyl dithiocarbamate, or mixtures thereof, and the like. Preferred dithiocarbamates are dipropyl dithiocarbamate, diisopropyl dithiocarbamate, dibutyl dithiocarbamate, diisobutyl dithiocarbamate, dicyclohexyl dithiocarbamate, diethylphenyl dithiocarbamate, di-2-ethylhexyl dithiocarbamate, or mixtures thereof. Dibutyl dithiocarbamate, dipropyl dithiocarbamate, dicyclohexyl dithiocarbamate, and di-2-ethylhexyl dithiocarbamate are particularly preferred, with dibutyl dithiocarbamate being most preferred.

Examples of various metal dithiophosphatealkylxanthate complexes that can be used in this invention are bis-(dibutyldithiophosphato diamylxanthato) Sn(IV), bis-(dipropyldithiophosphato dioctylxanthato) Sn(IV), bis-(di-2-ethylhexyldithiophosphato diethylhexylxanthato) Sn(IV), bis-(dioctyldithiophosphato di-2-ethoxyethylxanthato) Sn(IV), bis-(diethyldithiophosphato dibutylethylxanthato) Sn(IV), and the like. Bis-(dibutyldithiophosphato diamylxanthato) Sn(IV) and bis-(diethyldithiophosphato dibutoxyethylxanthato) Sn(IV) are preferred, with bis-(dibutyldithiophosphato diamylxanthato) Sn(IV) being most preferred.

Examples of various metal dithiophosphatedithiocarbamate complexes that can be used in this invention are bis-(diethyldithiophosphato dibutyldithiocarbamato) Sn(IV), bis-(dibutyldithiophosphato dibutyldithiocarbamato) Sn(IV), bis-(dipropyldithiophosphato dibutyldithiocarbamato) Sn(IV), bis-(diethyldithiophosphato di-2-ethylhexyldithiocarbamato) Sn(IV), bis-(di-2-ethylhexyldithiophosphato diethyldithiocarbamato) Sn(IV), and bis-(dioctyldithiophosphato diethyldithiocarbamato) Sn(IV). Preferred metal complexes are bis-(diethyldithiophosphato dibutyldithiocarbamato) Sn(IV), bis-(dibutyldithiophosphato dibutyldithiocarbamato) Sn(IV), bis(dipropyldithiophosphato dibutyldithiocarbamato) Sn(IV), and the like. Bis-(diethyldithiophosphato dibutyldithiocarbamato) Sn(IV), bis-(dibutyldithiophosphato dibutyldithiocarbamato) Sn(IV), bis-(di-2-ethylhexyldithiophosphato diethyldithiocarbamato) Sn(IV) are preferred, with bis-(diethyldithiophosphato dibutyldithiocarbamato) Sn(IV) being most preferred.

Examples of various metal dithiocarbamatealkylxanthate complexes that can be used in this invention are bis-(dibutyldithiocarbamato diamylxanthato) Sn(IV), bis-(dipropyldithiocarbamato dioctylxanthato) Sn(IV), bis-(dibutyldithiocarbamato dibutylxanthato) Sn(IV), bis-(dipropyldithiocarbamato diethylhexylxanthato) Sn(IV), bis-(dibutyldithiocarbamato-di-2-ethoxyethylxanthato) Sn(IV), bis(dibutyldithiocarbamato dibutoxyethylxanthato) Sn(IV), bis-(dipropyldithiocarbamato dibutoxyethylxanthato) Sn(IV), and bis-(diethyldithiocarbamato dibutoxyethylxanthato) Sn(IV). Preferred complexes are bis(dibutyldithiocarbamato diamylxanthato) Sn(IV), bis(dibutyldithiocarbamato dibutylxanthato) Sn(IV), and bis-(diethyldithiocarbamato dibutoxyethylxanthato) Sn(IV), or mixtures thereof, with bis-(dibutyldithiocarbamato diamylxanthato) Sn(IV) being most preferred.

The metal thiophosphate used in this invention preferably comprises a metal selected from the group consisting of Group IB, IIB, VIB, VIII of the Periodic Table, and mixtures thereof. A metal dithiophosphate is a preferred metal thiophosphate, with a metal dialkyldithiophosphate being particularly preferred. Copper, nickel, and zinc are particularly preferred metals, with zinc being most preferred. The alkyl groups preferably comprise from 3 to 10 carbon atoms. Particularly preferred metal thiophosphates are zinc dialkyldithiophosphates.

The amount of mixed ligand metal complex used in this invention need be only that which, in combination with the metal thiophosphate, is necessary to cause an enhancement in the antiwear performance of the oil. Typically, however, the concentration of the metal complex in the lubricating oil will range from about 0.05 to about 5 wt. %, preferably from about 0.1 to about 1.5 wt. %, of the oil. The concentration of the metal thiophosphate will range from about 0.1 to about 2 wt. %, preferably from about 0.15 to about 1 wt. %, of the lubricating oil.

Metal thiophosphates are commercially available from a number of vendors. As such, their method of manufacture is well known to those skilled in the art. The mixed ligand metal complexes can be prepared by the methods described in Examples 1 and 2 below.

The additives (or additive system) of this invention can be added directly to the lubricating oil. Often, however, they can be made in the form of an additive concentrate to facilitate handling and introduction of the additives into the oil. Typically, the concentrate will contain a suitable organic diluent and from about 10 to about 90 wt. %, preferably from about 30 to about 80 wt. %, of the additives. Suitable organic diluents include mineral oil, naphtha, benzene, toluene, xylene, and the like. The diluent should be compatible (e.g. soluble) with the oil and, preferably, substantially inert.

The lubricating oil (or concentrate) may also contain other additives known in the art such that a fully formulated oil is formed. Such additives include dispersants, other antiwear agents, antioxidants, corrosion inhibitors, detergents, pour point depressants, extreme pressure additives, viscosity index improvers and the like. These additives are typically disclosed, for example, in "Lubricant Additives" by C. V. Smalheer and R. Kennedy Smith, 1967, pp. 1-11 and in U.S. Pat. No. 4,105,571, the disclosures of which are incorporated herein by reference. These additives are present in proportions known in the art.

A lubricating oil containing the additive system of this invention can be used in essentially any application where wear protection is required. Thus, as used herein, "lubricating oil" (or "lubricating oil composition") is meant to include automotive lubricating oils, industrial oils, gear oils, transmission oils, and the like. In addition, the lubricating oil composition of this invention can be used in the lubrication system of essentially any internal combustion engine, including automobile and truck engines, two-cycle engines, aviation piston engines, marine and railroad engines, and the like. Also contemplated are lubricating oils for gas-fired engines, alcohol (e.g. methanol) powered engines, stationary powered engines, turbines, and the like.

This invention may be further understood by reference to the following examples which are not intended to restrict the scope of the claims.

Experimental Procedure

Valve train wear tests were performed in the following examples utilizing a Ford 2.3 liter engine with the pistons and connecting rods removed. The engine was driven by an 11.2 KW (15 horsepower) DC drive motor through a 1.2 timing belt drive. The engine was equipped with Oldsmobile valve springs 146.5–148.3 KG) to increase the load between the cam lobes and the followers. Oil and coolant were circulated using engine mounted pumps. All test runs were made at an oil and coolant temperature of 90°±2° C., an oil pressure of 330±8 kPa, and an engine speed of 1,000±8 rpm, with periodic stoppage for wear measurements.

During operation, wear occurs on the lobes of the cam shaft and followers due to the sliding contact. Cam lobe wear was determined using the sequence V-D test described in ASTM Test No. STP 315H-Part 3 (the disclosure of which is incorporated herein by reference) by measuring the "head-to-toe" dimension (cam base circle diameter plus maximum lift) at room temperature using a digital micrometer. The difference between the dimensions of new and used cam lobes is a measure of the individual cam lobe wear, usually measured to an accuracy within about 2 microns. The individual cam lobe wear values from all eight lobes on the camshaft were averaged to provide a single value of average cam lobe wear.)

EXAMPLE 1

Preparation of Bis-(Diethyldithiophosphato Dibutyldithiocarbamato) Sn(IV)

11.7 ml (0.1 mole) of stannic chloride was added to a magnetically stirred mixture of 48.6 g. (0.2 mole) of potassium dibutyldithiocarbamate in 500 ml of toluene under a nitrogen atmosphere. After stirring this mixture for two hours (during which time a white solid precipitated), 40.6 g. (0.2 mole) of ammonium diethyldithiophosphate was added and the stirring continued for another two hours. The mixture was then transferred to a separatory funnel, washed well with water, dried over anhydrous sodium sulfate, and filtered. The filtrate was concentrated to dryness under reduced pressure and subjected to vacuum for two hours. The yield of the viscous liquid product was 76.6 g. (88% conversion). Elemental analysis of the product gave the following results (in wt. %):

Found: C = 34.99; H = 6.35;
N = 3.12.
Calculated for $C_{26}H_{58}N_2O_4S_4P_2Sn$: C = 36.0; H = 6.47;
N = 3.23.

A portion of this product was used to formulate Oil D in Example 3 below.

EXAMPLE 2

Preparation of Bis-(Dibutyldithiocarbamato Diamylxanthato) Sn(IV)

Step 1

Synthesis of bis-dibutyldithiocarbamato Sn dichloride

A solution of 17.6 ml (0.15 mole) of stannic chloride in 200 ml of toluene was added to a stirred mixture of 72.9 g. (0.3 mole) of potassium dibutyldithiocarbamate in 400 ml of toluene. The resulting mixture was stirred for two hours, transferred to a separatory funnel, and then washed well with water. The toluene layer was dried over anhydrous sodium sulfate, filtered, and concentrated to dryness under reduced pressure. The residual solid was recrystallized from toluene-petroleum ether to yield 82.3 g. (91.7% conversion) of the resulting white solid. Elemental analysis of the product gave the following results:

Found: C=36.34; H=61.2;
N=4.79; S=22.56.
Calculated for $C_{18}H_{36}N_2S_4SnCl_2$: C=36.14; H=6.02;
N=4.68; S=21.4

Step 2

Synthesis of bis-(dibutyldithiocarbamato diamylxanthato) Sn(IV)

A solution of 32.3 g. of potassium amylxanthate in water was added to a stirred solution of 47.8 g. (0.08 mole) of the compound obtained in Step 1 in 400 ml of chloroform. After stirring the mixture for two hours, the mixture was transferred to a separatory funnel. The chloroform layer was separated. The water layer was extracted with chloroform. The chloroform solution and extract were combined, washed with water, dried over anhydrous sodium sulfate, and filtered. The filtrate was concentrated to dryness under reduced pressure. The residual solid was washed with petroleum ether and dried to give 43.6 g. of a light pale colored solid.

A portion of this product was used to formulate Oil C in Example 3 below.

EXAMPLE 3

Formulation of Test Oils

Test oils were formulated from the following two commercially available fully formulated reference lubricating oils from which the amount of antiwear additive (ZDDP) had been reduced until the oil contained about 0.02 wt. % phosphorus (which corresponds to about 0.25 wt. % ZDDP):

Oil A—an SF/CD 10W30 oil
Oil B—an SF/CC 10W30 oil

The test oils were as follows:
Oil C—Oil A+0.15 wt. % bis-(dibutyldithiocarbamato diethoxyethylxanthato) tin (IV)
Oil D—Oil B+0.15 wt diethyldithiophosphato) tin (IV)

EXAMPLE 4

Valve Train Wear Tests Using Oils A and C

Valve train wear tests were performed using Oils A and C. The average cam lobe wear in micrometers ($\mu$m) obtained during 60 hours of operation is shown in FIG. 1.

EXAMPLE 5

Valve Train Wear Tests Using Oils B and D

Valve train wear tests were also performed using Oils B and D. The average cam lobe wear in micrometers ($\mu$m) obtained during 60 hours of operation is shown in FIG. 2.

Figure 2:
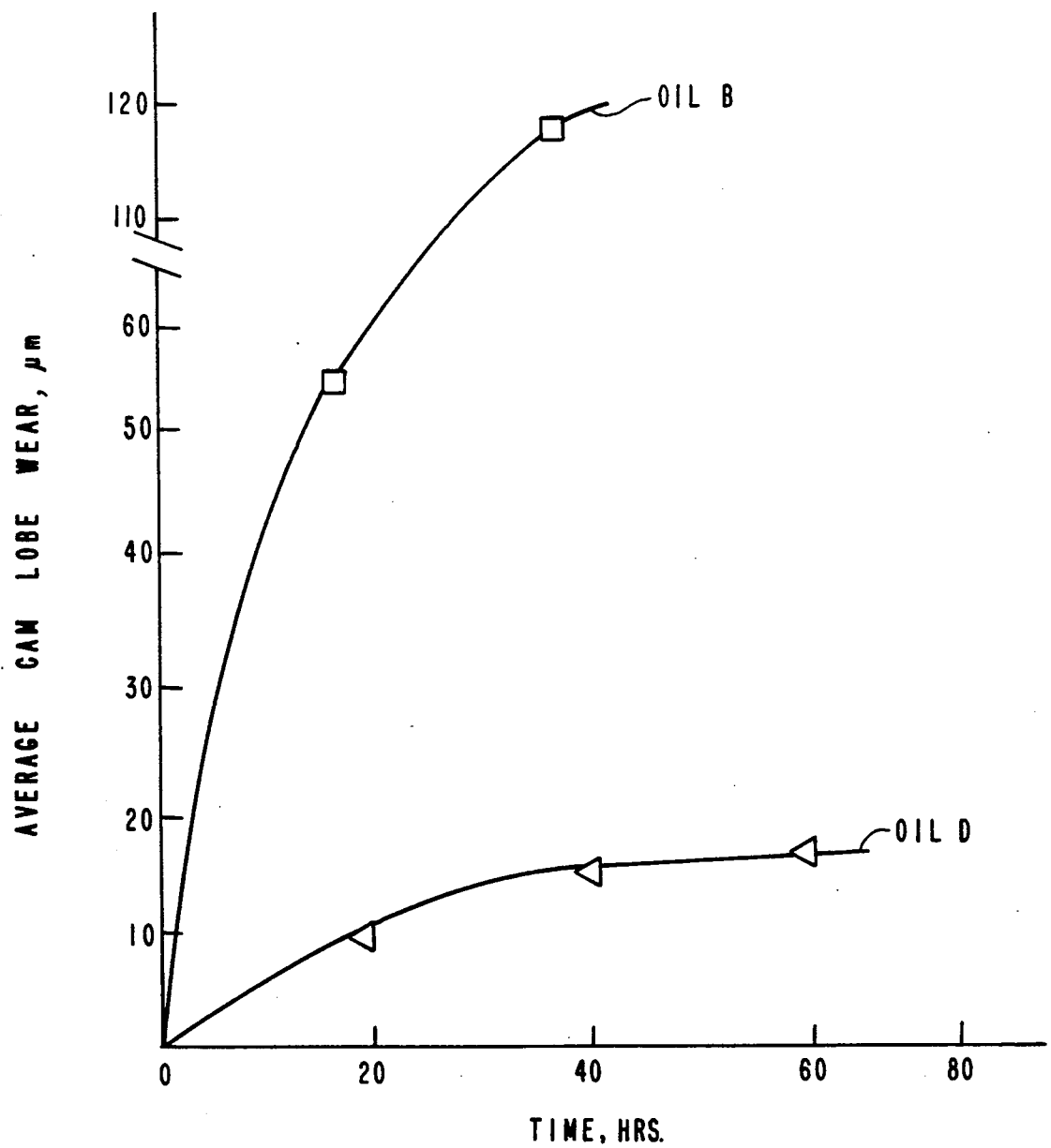

The data is FIGS. 1 and 2 show that engine wear is dramatically reduced when a mixed ligand metal complex and a metal thiophosphate are present in the lubricating oil. The data also show that this additive system allows the formulation of a lubricating oil having enhanced antiwear performance at phosphorus levels significantly below those of conventional oils.

What is claimed is:

1. A lubricating oil composition which comprises
    (a) a major amount of a lubricating oil basestock;
    (b) from about 0.05 to about 5 wt. % of at least one mixed ligand metal complex selected from the group consisting of
        (i) a metal dithiophosphate-alkylxanthate complex having the formula

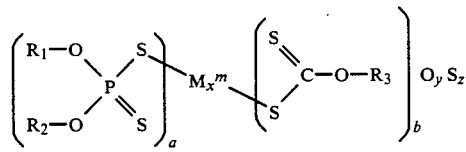

(ii) a metal dithiophosphate-dithiocarbamate complex having the formula

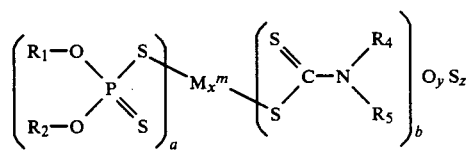

(iii) a metal dithiocarbamate-alkylxanthate complex having the formula

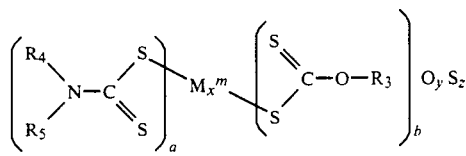

where
    $R_1$, $R_2$, $R_3$, $R_4$, and $R_5$ are each an alkyl group; an alkoxy substituted alkyl group; a polyalkoxy substituted alkyl group; an aryl group; or a substituted aryl group; having from 1 to 24 carbon atoms,
    M is a metal selected from the group consisting of antimony, bismuth, copper, iron, indium, molybdenum, tin, titanium, and zinc,
    a is an integer from 1 to 5,
    b is an integer from 1 to 5,
    m is an integer from 2 to 6,
    x is 1,
    y+z is an integer from 0 to 4; and
    (c) from about 0.1 to about 2 wt. % of a metal thiophosphate wherein the metal is selected from the group consisting of Group IB, IIB, VIB, VIII of the Periodic Table, and mixtures thereof.

2. The composition of claim 1 wherein at least one of $R_1$, $R_2$, $R_3$, $R_4$, and $R_5$ contains from 2 to 12 carbon atoms.

3. The composition of claim 2 wherein at least one of $R_1$, $R_2$, $R_3$, $R_4$, and $R_5$ contains from 2 to 8 carbon atoms.

4. The composition of claim 2 wherein M is antimony, molybdenum, tin, or zinc.

5. The composition of claim 4 wherein the metal thiophosphate comprises a metal dithiophosphate.

6. The composition of claim 5 wherein the metal in the metal dithiophosphate is copper, nickel, or zinc.

7. The composition of claim 6 wherein the metal in the metal dithiophosphate is zinc.

8. The composition of claim 1 wherein m is from 2 to 4.

9. A lubricating oil composition which comprises a major amount of a lubricating oil basestock and
    (a) from about 0.1 to about 1.5 wt. % of at least one mixed ligand metal complex comprising a complex selected from the group consisting of
        (i) a metal dithiophosphate-alkylxanthate complex having the formula

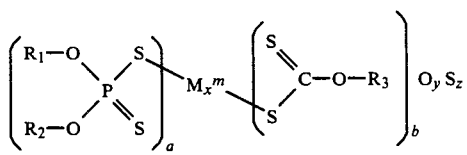

(ii) a metal dithiophosphate-dithiocarbamate complex having the formula

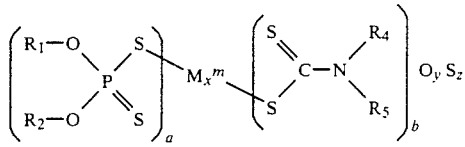

(iii) a metal dithiocarbamate-alkylxanthate complex having the formula

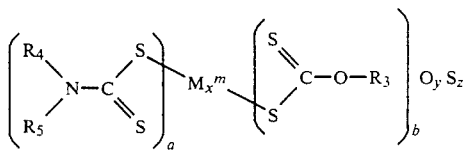

where
R$_1$, R$_2$, R$_3$, R$_4$, and R$_5$ are each an alkyl group, an alkoxy substituted alkyl group, a polyalkoxy substituted alkyl group, an aryl group, or a substituted aryl group, having from 2 to 8 carbon atoms,
M is antimony, molybdenum, tin, or zinc,
a is an integer from 1 to 5,
b is an integer from 1 to 5,
m is an integer from 2 to 6,
x is 1,
x+z is an integer from 0 to 4; and
(b) from about 0.15 to about 1 wt. % of a metal dialkyldithiophosphate wherein the metal in the metal dialkyldithiophosphate is copper, nickel, or zinc.

10. The composition of claim 9 wherein the substituted group in at least one of R$_1$, R$_2$, R$_3$, R$_4$, and R$_5$ contains at least one member selected from the group consisting of alkyl, aryl, hydroxy, alkylthio, amido, amino, keto, and ester groups.

11. The composition of claim 9 wherein the mixed ligand metal complex comprises a metal dithiophosphate-alkylxanthate complex selected from the group consisting of bis-(dibutyldithiophosphato diamylxanthato) Sn(IV), bis-(diethyldithiophosphato dibutoxyethylxanthato) Sn(IV), and mixtures thereof.

12. The composition of claim 11 wherein the metal in the metal dialkyldithiophosphate is zinc.

13. The composition of claim 12 wherein the metal dithiophosphate-alkylxanthate is bis-(dibutyldithiophosphato diamylxanthato) Sn(IV).

14. The composition of claim 9 wherein the mixed ligand metal complex comprises a metal dithiophosphatedithiocarbamate complex selected from the group consisting of bis-(diethyldiphosphato dibutyldithiocarbamato) Sn(IV), bis(dibutyldithiophosphato dibutyldithiocarbamato) Sn(IV), bis(di-2-ethylhexyldithiophosphato diethyldithiocarbamato) Sn(IV), and mixtures thereof.

15. The composition of claim 14 wherein the metal in the metal dialkyldithiophosphate is zinc.

16. The composition of claim 15 wherein the metal dithiophosphate-dithiocarbamate complex is bis-(diethyldithiophosphate dibutyldithiocarbamato) Sn(IV).

17. The composition of claim 9 wherein the mixed ligand metal complex comprises at least one metal dithiocarbamate-alkylxanthate complex selected from the group consisting of bis-(dibutyldithiocarbamato diamylxanthato) Sn(IV), bis(dibutyldithiocarbamato diamylxanthato) Sn(IV), bis-(diethyldithiocarbamato dibutoxyethylxanthato) Sn(IV), and mixtures thereof.

18. The composition of claim 17 wherein wherein the metal in the metal dialkyldithiophosphate is zinc.

19. The composition of claim 18 wherein the metal dithiocarbamate-alkylxanthate is bis-(dibutyldithiocarbamato diamylxanthato) Sn(IV).

20. A method for reducing the wear of an internal combustion engine which comprises lubricating the engine with the lubricating oil composition of claim 9.

21. An additive concentrate suitable for blending with lubricating oils to provide a lubricating composition having improved antiwear performance which comprises an organic diluent and from about 10 to about 90 wt. % of an additive system containing
(a) at least one mixed ligand metal complex selected from the group consisting of:
(i) a metal dithiophosphate-alkylxanthate complex having the formula

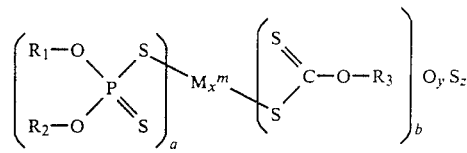

(ii) a metal dithiophosphate-dithiocarbamate complex having the formula

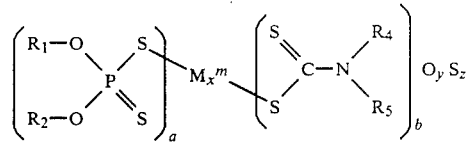

(iii) a metal dithiocarbamate-alkylxanthate complex having the formula

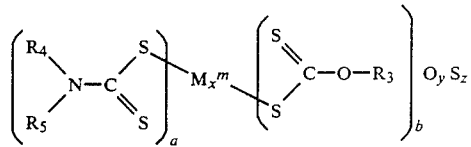

where
R$_1$, R$_2$, R$_3$, R$_4$, and R$_5$ are each an alkyl group; an alkoxy substituted alkyl group; a polyalkoxy substituted alkyl group; an aryl group; or a substituted aryl group; having from 1 to 24 carbon atoms,
M is a metal selected from the group consisting of antimony, bismuth, copper, iron, indium, molybdenum, tin, titanium, and zinc,
a is an integer from 1 to 5,
b is an integer from 1 to 5,
m is an integer from 2 to 6,
x is 1,
y+z is an integer from 0 to 4; and
(b) a metal thiophosphate wherein the metal is selected from the group consisting of Group IB, IIB, VIB, VIII of the Periodic Table, and mixtures thereof.

22. The concentrate of claim 21 wherein the organic diluent is mineral oil, naphtha, benzene, toluene, or xylene.

23. The concentrate of claim 22 wherein the organic diluent comprises a mineral oil in which the additive system is soluble.

24. The concentrate of claim 21 wherein at least one of $R_1$, $R_2$, $R_4$, and $R_5$ contains from 2 to 12 carbon atoms.

25. The concentrate of claim 21 wherein at least one of $R_1$, $R_2$, $R_4$, and $R_5$ contains from 2 to 8 carbon atoms.

26. The concentrate of claim 25 wherein the metal in the metal thiophosphate is copper, nickel, or zinc.

27. The concentrate of claim 26 wherein the metal in the metal thiophosphate is zinc.

28. The concentrate of claim 27 wherein wherein the mixed ligand metal complex comprises a metal dithiophosphatedithiocarbamate complex selected from the group consisting of bis-(diethyldiphosphato dibutyldithiocarbamato) Sn(IV), bis(dibutyldithiophosphato dibutyldithiocarbamato) Sn(IV), bis(di-2-ethylhexyldithiophosphato diethyldithiocarbamato) Sn(IV), and mixtures thereof.

29. The concentrate of claim 28 wherein the metal dithiophosphate-dithiocarbamate complex is bis-(diethyldithiophosphate dibutyldithiocarbamato) Sn(IV).

30. The concentrate of claim 27 wherein the mixed ligand metal complex comprises at least one metal dithiocarbamate-alkylxanthate complex selected from the group consisting of bis-(dibutyldithiocarbamato diamylxanthato) Sn(IV), bis(dibutyldithiocarbamato diamylxanthato) Sn(IV), bis-(diethyldithiocarbamato dibutoxyethylxanthato) Sn(IV), and mixtures thereof.

31. The concentrate of claim 30 wherein the metal dithiocarbamate-alkylxanthate is bis-(dibutyldithiocarbamato diamylxanthato) Sn(IV).

* * * * *